United States Patent [19]

Martin et al.

[11] Patent Number: 5,350,762
[45] Date of Patent: Sep. 27, 1994

[54] TETRAHYDROCYCLOPENT[B]INDOLE METHANAMINES AND RELATED COMPOUNDS

[75] Inventors: Lawrence L. Martin, Lebanon; Larry Davis, Sergeantsville, both of N.J.

[73] Assignee: Hoechst-Roussel Pharmaceuticals Incorporated, Somerville, N.J.

[21] Appl. No.: 28,110

[22] Filed: Mar. 8, 1993

[51] Int. Cl.$^5$ ............... C07D 209/80; C07D 413/02; A61K 31/40; A61K 31/535
[52] U.S. Cl. ..................... 514/411; 548/439; 548/449; 544/142; 544/372; 546/139; 546/200; 514/232.8; 514/253; 514/307; 514/320
[58] Field of Search ............... 548/439, 449; 514/411

[56] References Cited

U.S. PATENT DOCUMENTS

| | | | |
|---|---|---|---|
| 3,859,304 | 1/1975 | Dostert et al. | 514/411 |
| 4,009,181 | 2/1977 | Berger et al. | 514/411 |
| 4,128,560 | 12/1978 | Asselin et al. | 514/411 |
| 4,235,903 | 11/1980 | Dionne et al. | 514/411 |
| 5,100,891 | 3/1992 | Ong et al. | 514/232.8 |

OTHER PUBLICATIONS

Pugsley et al., Experentia vol. 33(1), pp. 57–59 (Jan. 1977).

Asselin et al., J. Med. Chem vol. 19(6), pp. 792–797 (Jun. 1976).

Humber, Demerson, Asselin, Charest, and Pelz; *Eur. J. Med. Chem.–Chimica* Therapeutica, May–Jun. 1975–10, No. 3, pp. 215–220.

*Primary Examiner*—Joseph Paul Brust
*Assistant Examiner*—Mary Susan H. Gabilan
*Attorney, Agent, or Firm*—Tatsuya Ikeda

[57] ABSTRACT

There are disclosed various compounds of the formula below,

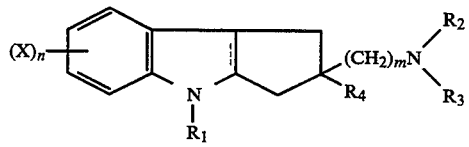

where the various parameters $R_1$, $R_2$, $R_3$, $R_4$, X, m and n are as defined in the specification, which show activities as a monoamine oxidase inhibitor demonstrating a utility for the treatment of depression, and activities as a cholinesterase inhibitor demonstrating a utility for the treatment of various memory dysfunctions such as Alzheimer's disease.

24 Claims, No Drawings

TETRAHYDROCYCLOPENT[B]INDOLE METHANAMINES AND RELATED COMPOUNDS

The present invention relates to compounds having Formula I depicted below, $$(I)$$

where,

R$_1$ is H, loweralkyl, arylloweralkyl or loweralkylcarbonyl;

R$_2$ is H, loweralkyl, aryl, arylloweralkyl or loweralkylcarbonyl;

R$_3$ is H or loweralkyl; and

R$_4$ is H or loweralkyl;

m is an integer of 1 or 2;

n is an integer of 1 or 2; and

X is H, loweralkyl, halogen, trifluoromethyl, nitro, loweralkoxy, arylloweralkoxy, $$-O-\overset{O}{\underset{\|}{C}}-N\underset{R_6}{\overset{R_5}{\diagup}},$$

amino, loweralkylamino, diloweralkylamino, loweralkylcarbonylamino or loweralkoxycarbonylamino, wherein R$_5$ is H or loweralkyl; and R$_6$ is H or loweralkyl, arylloweralkyl or aryl; or alternatively the group —NR$_5$R$_6$ as a whole is R$_7$ being hydrogen or loweralkyl; which compounds show activities as a monoamine oxidase inhibitor demonstrating a utility for the treatment of depression, and activities as a cholinesterase inhibitor demonstrating a utility for the treatment of various memory dysfunctions such as Alzheimer's disease.

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, isopropyl, n-butyl, iso-butyl, sec-butyl and straight- and branched-chain pentyl and hexyl.

The term aryl in each occurrence shall mean a phenyl group optionally mono-substituted with a loweralkyl, loweralkoxy, halogen, nitro or trifluoromethyl group.

The term halogen shall mean fluorine, chlorine, bromine or iodine.

The dotted lines appearing in various structural formulas in this specification and the appended claims shall mean an optional double bond.

Throughout the specification and the appended claims, a given chemical formula or name shall encompass all geometric, stereo, optical and tautomeric isomers where such isomers exist.

The compounds of this invention can be prepared by utilizing one or more of the synthetic steps described below.

Throughout the description of the synthetic steps, the notations X, m, n and R$_1$ through R$_7$ shall have the respective meanings given above unless otherwise stated indicated.

STEP A

A phenylhydrazine of Formula II where R$_8$ is hydrogen, loweralkyl, halogen, trifluoromethyl, nitro, loweralkoxy or arylloweralkoxy is allowed to react with a ketone of Formula III where R$_9$ is hydrogen or loweralkyl to undergo a Fischer indole synthesis reaction to afford a compound of Formula IV. Typically this reaction is conducted in a suitable medium such as 80% aqueous acetic acid at a temperature of about 100° C. For details of this Fischer indole synthesis reaction, the reader is referred for instance to Berger et al, U.S. Pat. No. 4,009,181.

STEP B

A compound of Formula (IVa) which is obtained from STEP A and is allowed to react with ethanol in a routine manner known to the art to afford a compound of Formula (IVb). This process step can be considered an alternative to STEP A above.

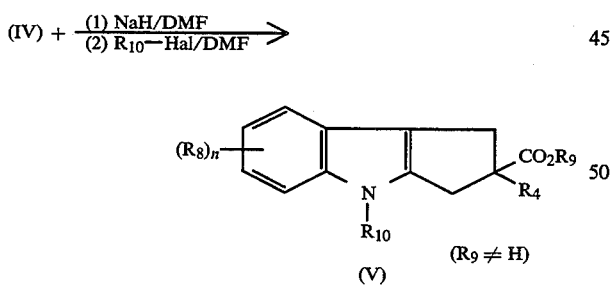

(IVa)

EtOH/HCl ⟶

(IVb)

STEP C

Compound IV is allowed to react with a strong base such as sodium hydride in a suitable medium such as dimethylformamide, and thereafter the resultant anion is allowed to react with a halide compound of formula $R_{10}$-Hal where $R_{10}$ is loweralkyl or arylloweralkyl and Hal is chlorine, bromine or iodine in a suitable medium such as dimethylformamide to afford a compound of Formula V.

$$(IV) + \frac{(1)\ NaH/DMF}{(2)\ R_{10}-Hal/DMF} \longrightarrow$$

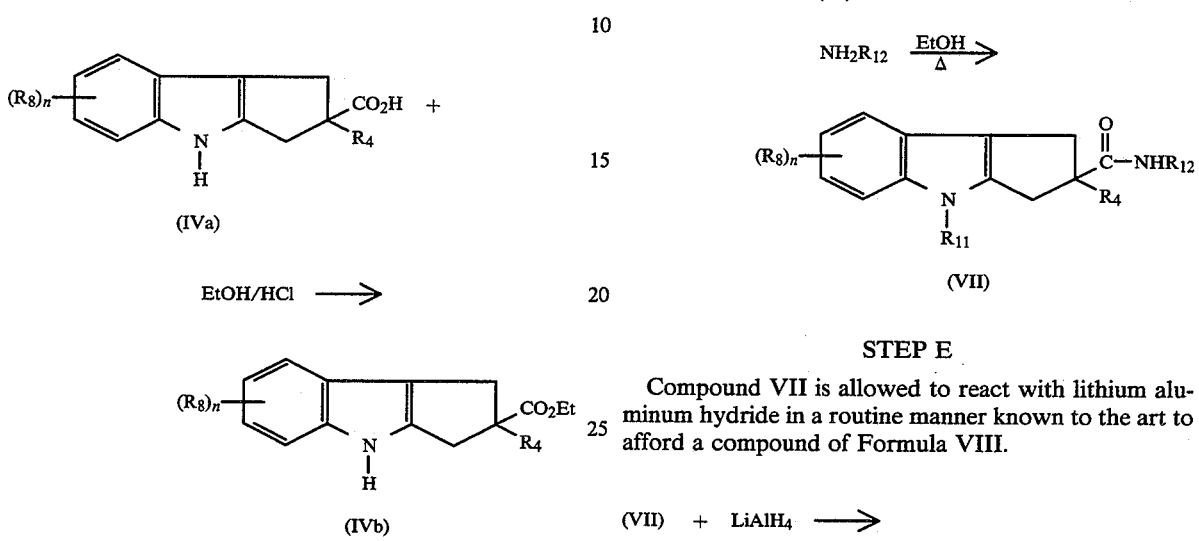

($R_9 \neq H$)

(V)

STEP D

A compound of Formula VI where $R_9$ is hydrogen or loweralkyl and $R_{11}$ is hydrogen, loweralkyl or arylloweralkyl which is obtained from one of the foregoing STEPS is allowed to react with ammonia or a primary amine of the formula $NH_2R_{12}$ where $R_{12}$ is hydrogen, loweralkyl, arylloweralkyl or aryl in a suitable solvent such as ethanol/$H_2O$ to afford a compound of Formula VII. It is convenient to conduct this reaction in a sealed tube.

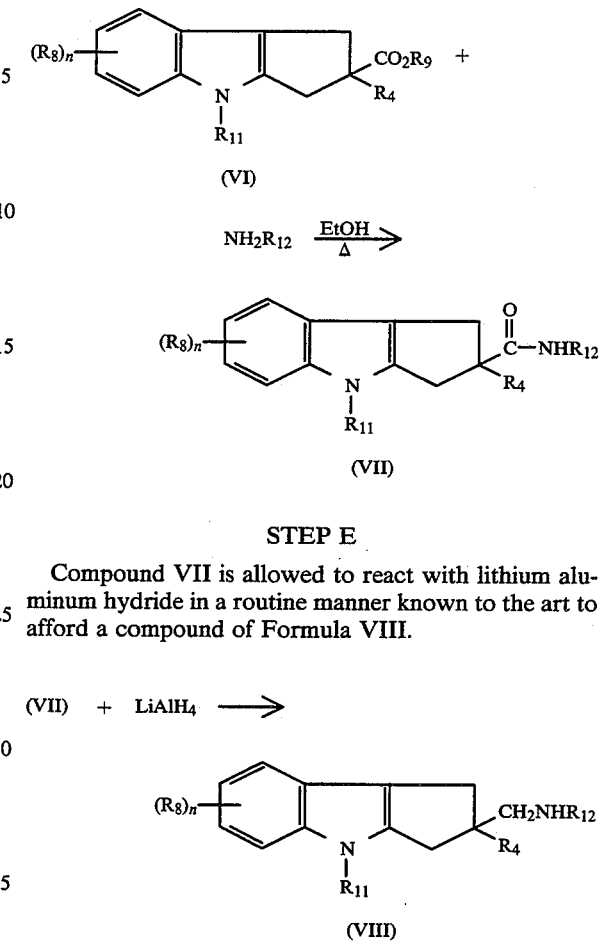

STEP E

Compound VII is allowed to react with lithium aluminum hydride in a routine manner known to the art to afford a compound of Formula VIII.

(VII) + LiAlH$_4$ ⟶

(VIII)

STEP F

A compound of Formula (Va) obtained from one of the foregoing STEPS is allowed to react with lithium aluminum hydride in a routine manner known to the art to afford a compound of Formula IX.

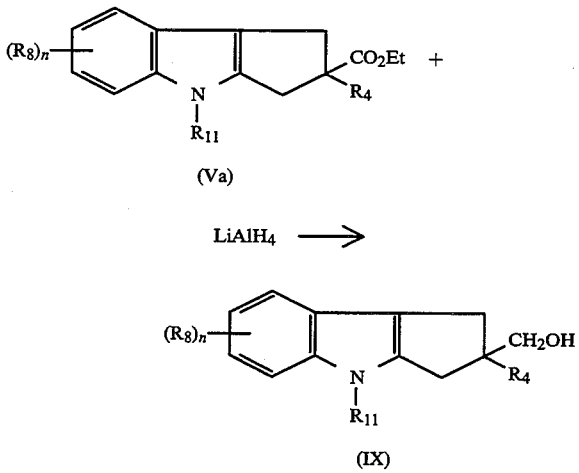

(Va)

LiAlH$_4$ ⟶

(IX)

STEP G

Compound IX is allowed to react with methanesulfonyl chloride (CH$_3$SO$_2$Cl) in a routine manner known to the art and the resultant mesylate is allowed to react with sodium cyanide in a routine manner known to the art to afford the corresponding nitrile. The latter is reduced with lithium aluminum hydride in a routine manner known to the art to afford a compound of Formula X.

(IX) + CH₃SO₂Cl ⟶

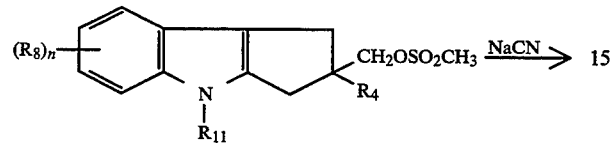
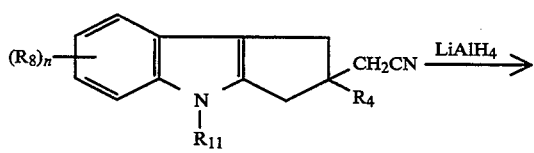
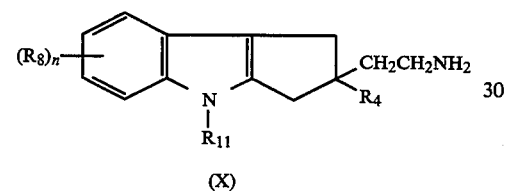

(X)

Typically, the second reaction step mentioned above is conducted in a suitable medium such as dimethylsulfoxide at a temperature of about 80°–120° C.

STEP H

Compound X is allowed to react with a halide compound of the formula R₁₂-Hal, where R₁₂ and Hal are as defined earlier, in a routine manner known to the art to afford a compound of Formula XI.

(X) + R₁₂—Hal ⟶

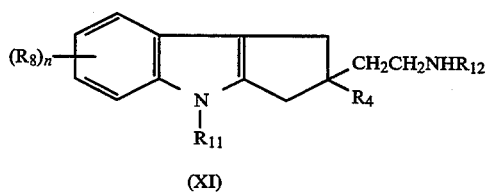

(XI)

STEP I

A compound of Formula XII which is obtained from one of the foregoing STEPS is allowed to react with a halide compound of the formula R₁₃-Hal where R₁₃ is loweralkyl and Hal is chlorine, bromine or iodine in a routine manner known to the art to afford a compound of Formula XIII.

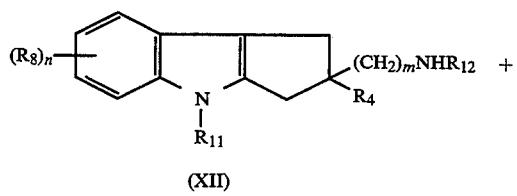

(XII)

R₁₃—Hal ⟶

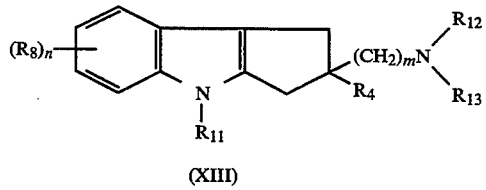

(XIII)

STEP J

As an alternative to the foregoing synthetic scheme, a compound of Formula (Vb) which is obtained from one of the foregoing STEPS is allowed to react with dicyclohexylcarbodiimide and an amine of the formula

(wherein R₂ and R₃ may not both be hydrogen; and R₂ is not loweralkylcarbonyl) in a routine manner known to the art to afford an amide compound and the latter is allowed to react with lithium aluminum hydride in a routine manner known to the art to afford a compound of Formula XIV.

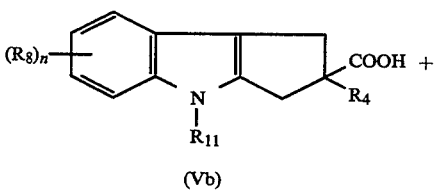

(Vb)

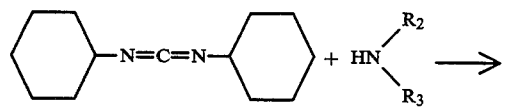

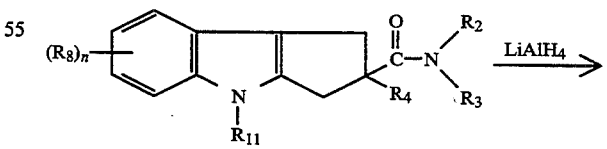

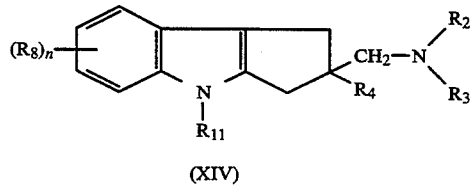

(XIV)

STEP K

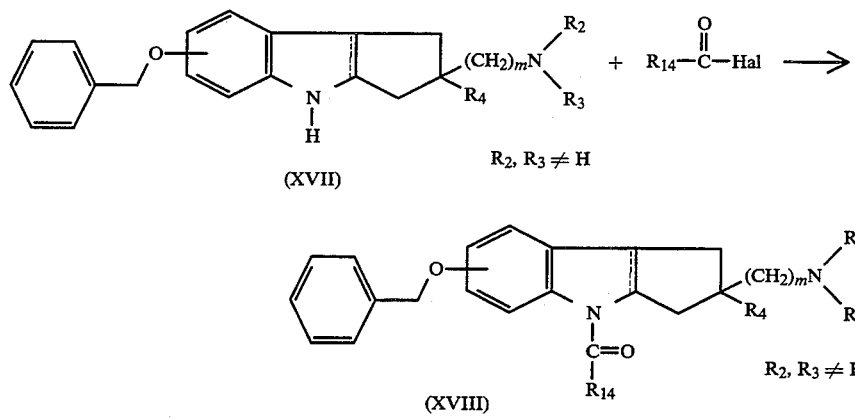

A compound of Formula XV which is obtained from one of the foregoing STEPS is allowed to react with sodium borohydride in the presence of trifluoroacetic acid in a routine manner known to the art (see, for instance, B. E. Maryanoff and D. F. McComsey, J. Org. Chem., 43, 2733-35 (1978)) to afford a compound of Formula XVI.

$R_{14}$ is loweralkyl to afford a compound of Formula XVIII in a routine manner known to the art.

STEP M

A compound of Formula XIX which is obtained from one of the foregoing STEPS is allowed to react with an acyl halide of the formula $R_{15}$CO-Hal where $R_{15}$ is loweralkyl in a routine manner known to the art to afford a compound of Formula XX.

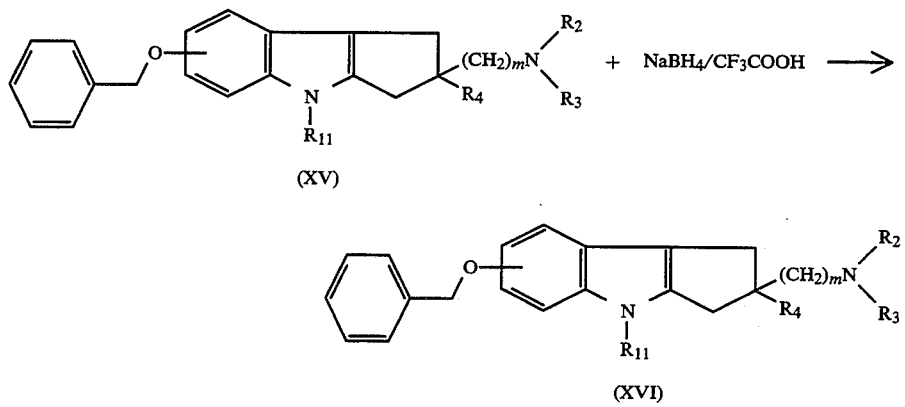

STEP L

A compound of Formula XVII which is obtained from one of the foregoing STEPS is allowed to react with an acyl halide of the formula $R_{14}$CO-Hal where

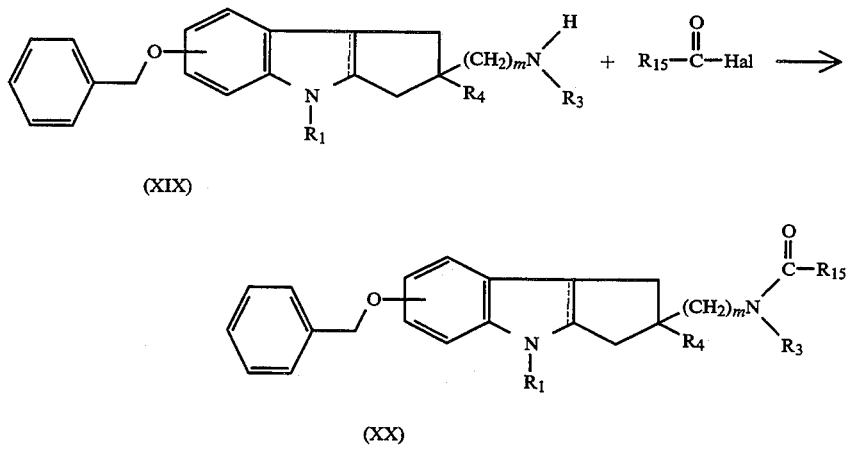

STEP N

A compound of Formula XXI (where $R_2$ may be hydrogen, loweralkyl, arylloweralkyl, aryl or loweralkylcarbonyl) which is obtained from one of the foregoing STEPS is allowed to undergo a hydrogenolysis reaction in a routine manner known to the art to afford a compound of Formula XXII. This reaction is typically conducted in the presence of a noble metal catalyst such as palladium under a suitable pressure of hydrogen gas.

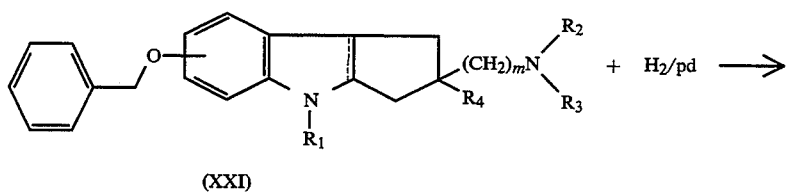

(XXI)

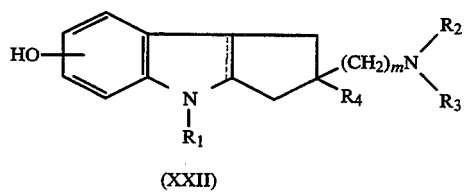

(XXII)

STEP O

Compound XXII is allowed to react with an isocyanate compound of the formula $R_5NCO$ in a routine manner known to the art to afford a compound of Formula XXIII.

(XXII) + $R_5NCO$ ⟶

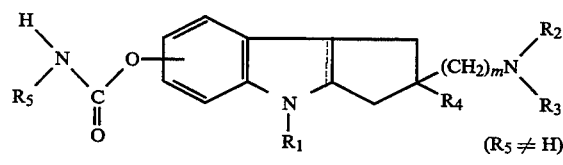

(XXIII)

STEP P

Compound XXIII is allowed to react with a strong base such as sodium hydride in a suitable medium and the resultant anion is allowed to react with a halide compound of $R_6$-Hal to afford a compound of Formula XXIV.

(XXIII) $\xrightarrow{\text{(1) NaH}}{\text{(2) }R_6\text{—Hal}}$

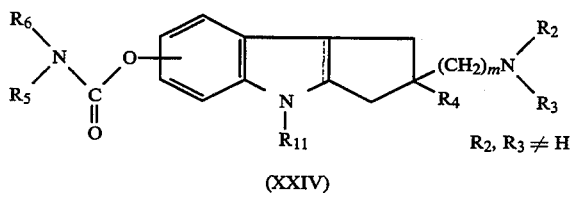

(XXIV)

STEP Q

As an alternative to the above, Compound XXII is allowed to react with 1,1'-carbonyldiimidazole and the resultant product is allowed to react with an amine of the formula $HNR_5R_6$ (where $R_5$ and $R_6$ are as defined at the beginning of the specification) to afford a compound XXIV.

(XXII) +

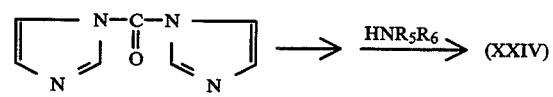 (XXIV)

STEP R

Where a compound of Formula I where X is amino, loweralkylamino or diloweralkylamino is desired, one starts out with a corresponding compound in which X is nitro and the compound is subjected to reduction to afford a corresponding amino compound and the amino compound is subjected to one or two alkylation reactions to afford a loweralkylamino compound or a diloweralkyl compound. All of these synthetic reactions are conducted in a routine manner known to the art.

Where a compound of Formula I where X is loweralkylcarbonylamino is desired, one starts out with the amino compound mentioned above and it is allowed to react with a loweralkylcarbonyl halide compound in a routine manner known to the art to afford a corresponding loweralkylcarbonyl compound.

The compounds of Formula I of this invention inhibit the activity of monoamine oxidase (an enzyme) and thereby increase the brain levels of biogenic amine(s). This activity is correlated with utility as an antidepressant. Methods used for determining this activity are described below.

Inhibition of Type A and Type B Monoamine Oxidase Activity in Rat Brain Synaptosomes Purpose To determine the selective inhibition of the two forms of monoamine oxidase (MAO).

Introduction

The metabolic deamination of amines has been known for over a hundred years, but more recently Johnston (1) described two forms of monoamine oxidase, which are called "type A" and "type B". The existence of the two forms is based on different substrate and inhibitor specificities. Serotonin (5HT) and norepinephrine (NE) are substrates for type A MAO, β-phenethylamine (PEA) and benzylamine are substrates for type B MAO, while dopamine (DA) and tyramine are substrates for both types. Clorgyline is a selective inhibitor of the type A enzyme, deprenyl and pargyline are selective inhibitors of the type B enzyme and tranylcypromine and iproniazid are nonselective inhibitors (2). It is recognized that MAO inhibitors have antidepressant properties.

Although various methods for measuring MAO activity are available, the described method involves the extraction of the radiolabeled deaminated metabolites of [$^3$H]-5HT or [$^{14}$C]-β-phenethylamine. This procedure allows MAO-A and MAO-B activities to be measured either simultaneously or individually (3).

Procedure

A. Reagents
1. Phosphate buffer (0.5M), pH 7.4:
   134.4 g $NaH_2PO_4.7H_2O$ bring to 1 liter in distilled $H_2O$ (A)
   17.3 g $Na_2HPO_4$ bring to 250 ml in distilled $H_2O$ (B)
   Adjust pH of A to 7.4 by slowly adding B (volumes as needed)
   Dilute 1:10 in distilled $H_2O$ (0.05M $PO_4$ buffer, pH 7.4)
2. 0.25M Sucrose ($PO_4$ buffered):
   21.4 g sucrose, bring to 250 ml with 0.05M $PO_4$ buffer
3. Substrate for MAO-A:
   a. Serotonin creatine $SO_4$ (5HT) is obtained from Sigma Chemical Company. A 5 mM stock solution is made up in 0.01 N HCl. This is used to dilute the specific activity of the [$^3$H]-5HT.
   b. [$^3$H]-5-Hydroxytryptamine creatinine sulfate (20–30 Ci/mmol) is obtained from New England Nuclear.
   c. Add 12 μl of [$^3$H]-5HT to 2 ml of the 5 mM 5HT solution. (Final amine concentration in the assay is 200 μM: see below.)
4. Substrate for MAO-B
   a. β-phenethylamine (PEA) is obtained from Sigma Chemical Company. A 5 mM stock solution is made up in 0.01 N HCl. This is used to dilute the specific activity of the [$^{14}$C]-PEA.
   b. β-[ethyl-1- $^{14}$C]-phenethylamine hydrochloride (40–50 mCi/mmol) is obtained from New England Nuclear.
   c. Add 12 μl of [$^{14}$C]-PEA to 2 ml of the 5 mM PEA solution. (Final amine concentration in the assay is 200 μM: see below.)
5. Equal amounts of MAO-A (5HT) and MAO-B (PEA) substrates are combined for simultaneously testing both MAO types, i.e. mixed stock solution of 2.5 mM 5HT and 2.5 mM PEA, 40 μl of this mixed solution gives a 200 μM final concentration of each amine in the assay. When testing only one MAO type, the individual 5 mM stock solutions must be diluted 1:1 with distilled water prior to adding 40 μl to the incubation mixture; i.e., same 200 μM final amine concentration.

B. Tissue Preparation

Male Wistar rats weighing 150–250 grams were sacrificed and the brains rapidly removed. Whole brain minus cerebellum was homogenized in 30 volumes of ice-cold, phosphate-buffered 0.25M sucrose, using a Potter-Elvejhem homogenizer. The homogenate was centrifuged at 1000 g for 10 minutes and the supernatant ($S_1$) decanted and recentrifuged at 18,000 g for 20 minutes. The resulting pellet ($P_2$) was resuspended in fresh 0.25M sucrose and served as the tissue source for mitochondrial MAO.

C. Assay
10 μl 0.5M $PO_4$ buffer, pH 7.4
50 μl $H_2O$ or appropriate drug concentration
400 μl Tissue suspension Tubes are preincubated for 15 minutes at 37° C. and the assay is started by adding 40 μl of combined substrate ([$^3$H]-5HT and [$^{14}$C]-PEA) at 15 second intervals. The tubes are incubated for 30 minutes at 37° C. and the reaction stopped by the addition of 0.3 ml 2N HCl. Tissue blank values are determined by adding the acid before the radioactive substrate. The oxidative products of the reaction are extracted with ethyl acetate/toluene (1:1). 5 ml of this mixture is added to the tubes. The resultant mixture is vortexed for 15 seconds to extract the deaminated metabolites into the organic phase and the latter is allowed to separate from the aqueous phase. The tubes are placed in acetone/dry ice bath to freeze the aqueous layer. When this layer is frozen, the top organic layer is poured into a scintillation vial. 10 ml of Liquiscint is added and the samples are counted using window settings for $^{14}$C in one channel and $^3$H in the second channel. $IC_{50}$ values are determined by log-probit analysis.

References

Johnston, J. P.: Some observations upon a new inhibitor of monoamine oxidase in brain tissue. Biochem. Pharmacol. 17: 1285–1297 (1968).

Fowler, C. J. and Ross, S. B.: Selective inhibitors of monoamine oxidase A and B: biochemical, pharmacological and clinical properties. Med. Res. Rev. 4: 323–328 (1984).

Kindt, M. V., Youngster, S. K., Sonsalia, P. K., Duvoisin, R. C. and Heikkila, R. E.: Role of monoamine oxidase-A (MAO-A) in the bioactivation and nigrostriatal dopaminergic neurotoxicity of the MPTP analog, 2'Me-MPTP. Eur. J. Pharmacol. 46:313:–318 (1988).

Results of the monoamine oxidase inhibition assay for representative compounds of this invention are presented in Table 1.

TABLE 1

| | Inhibitory Concentration - $IC_{50}$ (μM) | |
|---|---|---|
| Compound | Type-A | Type-B |
| 1,2,3,4-tetrahydro-4-methyl-7-methoxy-N-ethylcyclopent[b]indole-2-methanamine maleate | 182 | 713 |
| 1,2,3,4-tetrahydro-7-methoxy-4-methylcyclopent[b]indole-2-methanamine hydrochloride | 59 | 287 |
| (Reference Compounds) | | |
| Deprenyl | 0.14 | 0.016 |
| Tranylcypromine | 0.19 | 0.12 |

The compounds of Formula I of this invention also show ability to inhibit the activity of the enzyme acetylcholinesterase. This ability demonstrates utility of the compounds for the treatment of various memory dysfunctions characterized by a cholinergic deficit such as Alzheimer's Disease.

Cholinesterase Inhibition Assay

Cholinesterases are found throughout the body, both in the brain and in serum. However, only brain acetylcholinesterase (AChE) distribution is correlated with central cholinergic innervation. This same innervation is suggested to be weakened in Alzheimer's disease. We have determined in vitro inhibition of acetylcholinesterase activity in rat striatum.

In Vitro Inhibition of Acetylcholinesterase Activity in Rat Striatum

Acetylcholinesterase (AChE), which is sometimes called true or specific cholinesterase, is found in nerve cells, skeletal muscle, smooth muscle, various glands and red blood cells. AChE may be distinguished from other cholinesterases by substrate and inhibitor specificities and by regional distribution. Its distribution in brain roughly correlates with cholinergic innervation and subfractionation shows the highest level in nerve terminals.

It is generally accepted that the physiological role of AChE is the rapid hydrolysis and inactivation of acetylcholine. Inhibitors of AChE show marked cholinomimetic effects in cholinergically-innervated effector organs and have been used therapeutically in the treatment of glaucoma, myasthenia gravis and paralytic ileus. However, recent studies have suggested that AChE inhibitors may also be beneficial in the treatment of Alzheimer's disease.

The method described below was used in this invention for assaying cholinesterase activity. This is a modification of the method of Ellman et al., Biochem. Pharmacol. 7,88 (1961).

Procedure

A. Reagents 1. 0.05M Phosphate buffer, pH 7.2
   (a) 6.85 g NaH$_2$PO$_4$.H$_2$O/100 ml distilled H$_2$O
   (b) 13.40 g Na$_2$HPO$_4$.7H$_2$O/100 ml distilled H$_2$O
   (c) add (a) to (b) until pH reaches 7.2
   (d) Dilute 1:10
2. Substrate in buffer
   (a) 198 mg acetylthiocholine chloride (10 mM)
   (b) bring to 100 ml with 0.05M phosphate buffer, pH 7.2 (reagent 1)
3. DTNB in buffer
   (a) 19.8 mg 5,5-dithiobisnitrobenzoic acid (DTNB) (0.5 mM)
   (b) bring to 100 ml with 0.05M phosphate buffer, pH 7.2 (reagent 1)
4. A 2 mM stock solution of the test drug is made up in a suitable vehicle and brought to volume with distilled water. Drugs are serially diluted (1:10) with 0.5 mM DTNB (reagent 3) such that the final concentration of drug (in cuvette) is $10^{-4}$M and screened for activity. If active, IC$_{50}$ values are determined from the inhibitory activity of subsequent concentrations.

B. Tissue Preparation

Male Wistar rats are decapitated, brains rapidly removed, corpora striata dissected free, weighed and homogenized in 19 volumes (approximately 7 mg protein/ml) of 0.05M phosphate buffer, pH 7.2 using a Potter-Elvejhem homogenizer. A 25 microliter aliquot of the homogenate is added to 1.0 milliter buffer/DTNB/vehicle with and without the various concentrations of the test drug and preincubated for 10 minutes at 37° C.

C. Assay

Enzyme activity is measured with the Beckman DU-50 spectrophotometer. This method can be used for IC$_{50}$ determinations and for measuring kinetic constants.

Instrument Settings
Kinetics Soft-Pac Module #598273 (10)
Program #6 Kindata:
  Source—Vis
  Wavelength—412 nm
  Sipper—none
  Cuvettes—2 ml cuvettes using auto 6-sampler
  Blank—1 for each substrate concentration
  Interval time—15 seconds (15 or 30 seconds for kinetics)
  Total time—5 minutes (5 or 10 minutes for kinetics)
  Plot—yes
  Span—autoscale
  Slope—increasing
  Results—yes (gives slope)
  Factor—1

Reagents are added to the blank and sample cuvettes as follows:

| | |
|---|---|
| Blank: | 0.8 ml Phosphate Buffer/DTNB |
| | 0.8 ml Buffer/Substrate |
| Control: | 0.8 ml Phosphate Buffer/DTNB/Enzyme |
| | 0.8 ml Phosphate Buffer/Substrate |
| Drug: | 0.8 ml Phosphate Buffer/DTNB/Drug/Enzyme |
| | 0.8 ml Phosphate Buffer/Substrate |

Blank values are determined for each run to control for non-enzymatic hydrolysis of substrate and these values are automatically subtracted by the kindata program available on kinetics soft-pac module. This program also calculates the rate of absorbance change for each cuvette.

For IC$_{50}$ Determinations:

Substrate concentration is 10 mM diluted 1:2 in assay yielding final concentration of 5 mM. DTNB concentration is 0.5 mM yielding 0.25 mM final concentration.

$$\% \text{ Inhibition} = \frac{\text{slope control} - \text{slope drug}}{\text{slope control}} \times 100$$

IC$_{50}$ values are calculated from log-probit analysis

Results of this assay for some of the compounds of this invention and physostigmine (reference compound) are presented in Table 2.

TABLE 2

| Compound | IC$_{50}$ (μM) |
|---|---|
| 1,2,3,4-Tetrahydro-2-[(dimethylamino)methyl]-4-methylcyclopent[b]indol-7-yl methylcarbamate hydrochloride (Reference Compound) | 9.6 |
| Physostigmine | 0.034 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric, 2-naphthalenesulfonic and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
1,2,3,4-tetrahydro-7-methoxy-4-methylcyclopent[b]indole-2-methanamine;
1,2,3,4-tetrahydro-7-phenylmethoxy-4-methylcyclopent[b]indole-2-methanamine;
1,2,3,4-tetrahydro-7-methoxy-N-methylcyclopent[b]indole-2-methanamine;
1,2,3,4-tetrahydro-7-methoxy-N,4-dimethylcyclopent[b]indole-2-methanamine;
1,2,3,4-tetrahydro-7-phenylmethoxy-N,4-dimethylcyclopent[b]indole-2-methanamine;
1,2,3,4-tetrahydro-4-methyl-2-[(methylamino)methyl]-cyclopent[b]indol-7-ol;
1,2,3,4-tetrahydro-4-methyl-2-[(methylamino)methyl]-cyclopent[b]indol-7-yl methylcarbamate;
1,2,3,4-tetrahydro-7-methoxy-N,N,4-trimethylcyclopent[b]indole-2-methanamine;
1,2,3,4-tetrahydro-7-phenylmethoxy-N,N,4-trimethylcyclopent[b]indole-2-methanamine;
1,2,3,4-tetrahydro-4-methyl-2-[(dimethylamino)methyl]cyclopent[b]indole-7-ol;
1,2,3,4-tetrahydro-2-[(dimethylamino)methyl]-4-methylcyclopent[b]indol-7-yl methylcarbamate;
1,2,3,4-tetrahydro-4-methyl-7-methoxy-N-ethylcyclopent[b]indole-2-methanamine;
1,2,3,4-tetrahydro-7-methoxy-N-propylcyclopent[b]indole-2-methanamine;
1,2,3,4-tetrahydro-N,4-dimethyl-N-propyl-7-methoxycyclopent[b]indole-2-methanamine;
and
1,2,3,4-tetrahydro-7-phenylmethoxy-4-methylcyclopent[b]indole-2-ethaneamine.

EXAMPLE 1

1,2,3,4,-Tetrahydro-7-methoxycyclopent[b]indole-2-carboxylic acid

To 250 ml of 80% acetic acid in water were added 4-methoxyphenylhydrazine hydrochloride (21 g, 0.12 mole) and 3-oxocyclopentane carboxylic acid (20 g, 0.15 mole). After stirring at ambient temperature for two hours, the mixture was stirred at 100° C. for three hours. After cooling, the mixture was filtered, and the tan precipitate washed with water, and dried to give 15 g of a solid, mp ~200° C. A sample of this material was recrystallized from ethanol/ether (1:2) to give a tan solid, mp 210° C. (dec.).

Analysis: Calculated for $C_{13}H_{13}NO_3$: 67.52%C 5.67%H 6.06%N Found: 67.28%C 5.77%H 5.94%N

EXAMPLE 2

1,2,3,4-Tetrahydro-7-methoxycyclopent[b]indole-2-carboxylic acid ethyl ester

To a suspension of 1,2,3,4-tetrahydro-7-methoxycyclopent[b]indole-2-carboxylic acid (10 g, 0.043 mole) in 100 ml of absolute ethanol, was added 3 ml of ethereal HCl solution, and the mixture was stirred at ambient temperature for twenty hours. The mixture was concentrated to a brown oil (10 g), which was eluted on a silica gel column with 1% ethyl acetate/dichloromethane via HPLC. The desired fractions were combined and concentrated to afford a brown oil, which solidified on cooling to give 8.0 g of a lavender solid, mp 82°–3° C.

Analysis: Calculated for $C_{15}H_{17}NO_3$: 69.48%C 6.61%H 5.40%N Found: 69.08%C 6.53%H 5.19%N

EXAMPLE 3

1,2,3,4-Tetrahydro-4-methyl-7-methoxycyclopent[b]indole-2-carboxylic acid ethyl ester To a solution of 1,2,3,4-tetrahydro-7-methoxycyclopent[b]indole-2-carboxylic acid ethyl ester (10 g, 0.04 mole) in 75 ml of dimethylformamide, was added sodium hydride (1.7 g, 60% in oil, 0.043 mole). After stirring at ambient temperature for two hours, a solution of methyl iodide (2.7 ml, 0.043 mole) in dimethylformamide (10 ml) was added, and the mixture was stirred at 70° C. for five hours. After cooling, the mixture was poured into 200 ml of water, stirred for five minutes, and extracted with ethyl acetate. The organic layer was washed successively with water (2×) and a saturated NaCl solution, and then dried over anhydrous MgSO4. After filtering, the solvent was evaporated to afford a dark oil (~10 g) which was eluted on a silica gel column with dichloromethane via HPLC. The desired fractions were combined and concentrated to give the product as a thick yellow oil, 6.8 g.

Analysis: Calculated for $C_{16}H_{19}NO_3$: 70.31%C 7.01%H 5.12%N Found: 70.09%C 6.86%H 5.19%N

EXAMPLE 4

1,2,3,4-Tetrahydro-7-methoxy-4-methylcylopent[b]indole-2-carboxylic acid

To a solution of 1,2,3,4-tetrahydro-7-methoxy-4-methylcyclopent[b]indole-2-carboxylic acid ethyl ester (6.2 g, 0.023 mole) in 25 ml of ethanol, was added dimethylamine (40% aqueous solution, 10 ml, 0.09 mole). After stirring at 100° C. in a sealed tube for four days, the solution was concentrated to a brown oil (~6 g), which was eluted on a silica gel column with 20% methanol/ethyl acetate via HPLC. The desired fraction was concentrated to a tan solid, 5.0 g, m.p. 162°–164° C.

Analysis: Calculated for $C_{14}H_{15}NO_3$: 68.55%C 6.16%H 5.71%N Found: 68.13%C 6.37%H 5.67%N

EXAMPLE 5

1,2,3,4-Tetrahydro-7-phenylmethoxycyclopent[b]indole-2-carboxylic acid ethyl ester To 250 ml of 80% acetic acid in water, were added 4-phenylmethoxyphenylhydrazine hydrochloride (30 g, 0.12 mole) and 3-oxocyclopentane carboxylic acid ethyl ester (20 g, 0.13 mole). After stirring at ambient temperature for one hour and then at 100° C. for four hours, the mixture was cooled and poured into one liter of water. After stirring for five minutes, the mixture was extracted with ethyl acetate (3×). The organic layer was washed successively with water (2×) and saturated sodium chloride solution, and thereafter dried over anhydrous MgSO4. After filtering, the solution was concentrated to a dark oil (~48 g), which was eluted on a silica gel column with 5% ethyl acetate/dichloromethane via HPLC. The desired fractions were combined and concentrated to give the product as a thick brown oil (24.1 g).

Analysis: Calculated for $C_{21}H_{21}NO_3$: 75.20%C 6.31%H 4.18%N Found: 74.94%C 6.22%H 4.13%N

EXAMPLE 6

1,2,3,4-Tetrahydro-7-phenylmethoxy-4-methylcyclopent[b]indole-2-carboxylic acid ethyl ester To a suspension of sodium hydride (60% in oil, 3.0 g, 0.075 mole) in 25 ml of dry dimethylformamide, was added a solution of 1,2,3,4-tetrahydro-7-phenylmethoxycyclopent[b]indole-2-carboxylic acid ethyl ester (23.5 g, 0.07 mole) in 100 ml of dry dimethylformamide. After stirring at ambient temperature for two hours, a solution of methyl iodide (4.7 ml, 0.075 mole) in 20 ml of dimethylformamide was added, and the mixture was stirred at 70° C. for five hours. After cooling, the mixture was poured into 500 ml of water, stirred for five minutes, and then extracted with ethyl acetate (3×). The organic layer was washed successively with water and saturated sodium chloride solution, and dried over anhydrous MgSO4. After filtering, the solvent was evaporated to afford a brown oil (~25 g), which was eluted on a silica gel column with 5% ethyl acetate/dichloromethane via HPLC. The desired fraction was concentrated to a thick brown oil, 20.6 g, which solidified on cooling, m.p. 90°–95° C. A sample of this material was recrystallized from ethanol to give the product as an off-white solid, m.p. 109°–110° C.

Analysis: Calculated for $C_{22}H_{23}NO_3$: 75.62%C 6.63%H 4.01%N Found: 75.47%C 6.81%H 3.92%N

EXAMPLE 7

1,2,3,4-Tetrahydro-7-phenylmethoxycyclopent[b]indole-2-carboxylic acid

To 100 ml of 80% acetic acid in water, was added 1,2,3,4-tetrahydro-7-phenylmethoxycyclopent[b]indole-2-carboxylic acid ethyl ester (10 g, 0.03 mole). After stirring at 100° C. for four hours, the mixture was cooled, poured into 500 ml of water, stirred for five minutes, and extracted with ethyl acetate (3×). The organic layer was washed successively with water and saturated sodium chloride solution, and thereafter dried over anhydrous MgSO4. After filtering, the solution was concentrated to a dark oil (~10 g), which was eluted on a silica gel column with 5% ethyl acetate/dichloromethane via HPLC. The desired fractions were combined and concentrated to a tan solid, 1.3 g, m.p. 160°–162° C. This material was recrystallized from ether to give the product as a tan solid, 1.0 g, m.p. 161°–163° C.

Analysis: Calculated for $C_{19}H_{17}NO_3$: 74.25%C 5.58%H 4.56%N Found: 74.45%C 5.60%H 4.45%N

EXAMPLE 8

1,2,3,4-Tetrahydro-7-methoxy-4-methylcyclopent[b]indole-2-carboxylic acid amide To a reaction tube were added ammonia (30% aqueous solution, 10 ml, 0.17 mole) and a solution of 1,2,3,4-tetrahydro-7-methoxy-4methylcyclopent[b]-2-carboxylic acid ethyl ester (4.0 g, 0.015 mole) in 25 ml of absolute ethanol. After stirring at 100° C. for six days, the mixture was concentrated to a brown semi-solid, which was triturated with ethanol/ether (1:10) to give 3.0 g of the product as a tan precipitate, m.p. 178°–180° C.

Analysis: Calculated for $C_{14}H_{16}N_2O_2$: 68.83%C 6.60%H 11.47%N Found: 68.51%C 6.58%H 11.10%N

EXAMPLE 9

1,2,3,4-Tetrahydro-7-phenylmethoxy-4-methylcyclopent[b]indole-2-carboxylic acid amide In a sealed tube was added a solution of 1,2,3,4-tetrahydro-7-phenylmethoxy-4-methylcyclopent[b]indole-2-carboxylic acid ecid ethyl ester (5.0 g, 0.014 mole) in 25 ml of absolute ethanol, followed by ammonia (30% aqueous solution, 10ml, 0.17 mole). After heating at 100° C. for five days, the mixture was cooled and the resultant tan precipitate collected and dried to give 3.0 g, m.p. 145°–148° C.

EXAMPLE 10

1,2,3,4-Tetrahydro-7-methoxy-N-methylcyclopent[b]indole-2-carboxylic acid amide 1,2,3,4-tetrahydro-7-methoxycyclopent[b]indol-2-carboxylic acid ethyl ester (10.0 g, 0.039 mole) was added to a solution of methyl amine (6.0 g, 0.19 mole) and 40 ml of ethanol in a sealed tube. The mixture was heated to 100° C. and stirred for 96 hours. The mixture was concentrated to yield a brown solid (10.4 g), which was triturated with 50% ethyl acetate in $CH_2Cl_2$ to yield a tan solid (3.3 g). A portion (1.5 g) of this material was recrystallized from acetonitrile to yield 1.1 g of the product as a tan solid, m.p. 191°–193° C.

Analysis: Calculated for $C_{14}H_{16}N_2O_2$: 68.83%C 6.60%H 11.47%N Found: 68.98%C 6.67%H 11.69%N

EXAMPLE 11

1,2,3,4-Tetrahydro-7-methoxy-N,4-dimethylcyclopent[b]indole-2-carboxylic acid amide To a solution of 1,2,3,4-tetrahydro-4-methyl-7-methoxycyclopent[b]indole-2-carboxylic acid ethyl ester (4.5 g, 0.016 mole) in 100 ml of absolute ethanol, was added methylamine (40% aqueous solution, 15 ml, 6 g, 0.18 mole). The mixture was stirred at 70° C. for 50 hours in a sealed tube. The mixture was concentrated to a brown solid (~5 g) which was eluted on a silica gel column with ethyl acetate/dichloromethane (1:1) via HPLC. The desired fractions were combined and concentrated to a white solid, 3.0 g, mp 164°–165° C. A sample of this material was recrystallized from ethanol to afford the product as a white solid, mp 166°–167° C.

Analysis: Calculated for $C_{15}H_{18}N_2O_2$: 69.74%C 7.02%H 10.85%N Found: 69.30%C 7.13%H 10.75%N

EXAMPLE 12

1,2,3,4-Tetrahydro-7-phenylmethoxy-N,4-dimethylcyclopent[b]indole-2-carboxylic acid amide In a 50 ml sealed tube, was added a solution of 1,2,3,4-tetrahydro-7-phenylmethoxy-4-methylcyclopent[b]indole-2-carboxylic acid ethyl ester (10 g, 0.03 mole) in 25 ml absolute ethanol, followed by methylamine (40% aqueous solution, 10 ml, 0.13 mole). After stirring at 100° C. for six days, the mixture was cooled. A tan solid precipitated, which was collected and dried to give 7.0 g of the product as a solid, m.p. 176°–177° C. A sample of this solid was recrystallized from ethanol/ether (1:1) to give white crystals, m.p. 181°–182° C.

Analysis:

Calculated for $C_{21}H_{22}N_2O_2$: 75.42%C 6.63%H 8.38%N Found: 75.44%C 6.76%H 8.39%N

EXAMPLE 13

1,2,3,4-Tetrahydro-7-methoxy-N,N4-trimethylcyclopent[b]indole-2-carboxylic acid amide To 100 ml of dichloromethane was added 1,2,3,4-tetrahydro-7-methoxy-4-methylcyclopent[b]carboxylic acid (4.5 g, 0.018 mole), dimethylamine (40% aqueous solution, 2 ml, 0.018 mole), and dicyclohexylcarbodiimide (4.0 g, 0.02 mole). After stirring at ambient temperature for two days, the mixture was filtered, and the filtrate concentrated to afford a brown oil (~8 g). This oil was eluted on a silica gel column with ethyl acetate via HPLC. The desired fraction was concentrated to give the product as an off-white solid, 2.0 g, m.p. 116°–118° C.

Analysis: Calculated for $C_{16}H_{20}N_2O_2$: 70.56%C 7.40%H 10.29%N Found: 70.33%C 7.48%H 9.98%N

EXAMPLE 14

1,2,3,4-Tetrahydro-4-methyl-7-methoxy-N-ethylcyclopent[b]indole-2-carboxylic acid amide In a 50 ml sealed tube was dissolved 1,2,3,4-tetrahydro-4-methyl-7-methoxycyclopent[b]indole-2-carboxylic acid ethyl ester (2.8 g, 0.01 mole)in 25 ml of ethanol. To this was added an aqueous solution of ethylamine (70% solution, 5 ml, 0.075 mole). After stirring at 90° C. for five days, the mixture was concentrated to a brown solid, (~3 g) which was eluted on a silica gel column with ethyl acetate/dichloromethane (1:2) via HPLC. The desired fractions were combined to yield 1.3 g of a white solid, m.p. 162°–3° C. A sample of this material (0.5 g) was recrystallized from ethyl acetate/ether (1:10) to give the product as white crystals, 0.4 g, m.p. 163°–4° C.

Analysis: Calculated for $C_{16}H_{20}N_2O_2$: 70.56%C 7.40%H 10.29%N Found: 70.36%C 7.27%H 10.31%N

EXAMPLE 15

1,2,3,4-Tetrahydro-7-methoxy-N-propylcyclopent[b]indole-2-carboxylic acid amide 1,2,3,4-Tetrahydro-7-methoxycyclopent[b]indol-2-carboxylic acid ethyl ester (9.5 g, 0.037 mole) was added to n-propyl amine (30 ml) in a sealed tube and heated to 100° C. with stirring for 26 hours. The mixture was then concentrated to yield a brown oil (12.4 g), which was eluted with 10% ethyl acetate in $CH_2Cl_2$ and then with 50% ethyl acetate in $CH_2Cl_2$ on a silica gel column via HPLC. The desired fractions were concentrated to yield the product as a tan solid 6.5 g, mp 141°–143° C. A portion of this material (1.2 g) was recrystallized from ether in ethyl acetate (5:1) to yield the product as a white solid, 0.8 g, mp 141°–143° C.

Analysis: Calculated for $C_{16}H_{20}N_2O_2$: 70.56%C 7.40%H 10.29%N Found: 70.72%C 7.44%H 10.27%N

EXAMPLE 16

1,2,3,4-Tetrahydro-7-methoxy-4-methylcyclopent[b]indole-2 -methanol

To a solution of 1,2,3,4-tetrahydro-7-methoxy-4-methylcyclopent[b]indole-2-carboxylic acid ethyl ester (2.0 g, 0.007 mole) in 30 ml of dry tetrahydrofuran, was added lithium aluminum hydride (1M solution in tetrahydrofuran, 15 ml, 0.015 mole). After stirring at reflux for three hours, the mixture was cooled, quenched with 5 ml of saturated ammonium chloride solution and then diluted with 50 ml of ether. The mixture was filtered, and the filtrate concentrated to a yellow oil (~2 g). This oil was eluted on a silica gel column with 10% ethyl acetate/dichloromethane via HPLC. The desired fractions were combined and concentrated to give the product as a thick yellow oil (1.2g).

Analysis: Calculated for $C_{14}H_{17}NO_2$: 72.70%C 7.41%H 6.06%N Found 72.61%C 7.50%H 5.93%N

EXAMPLE 17

1,2,3,4-Tetrahydro-7-phenylmethoxy-4-methycyclopent[b]indole-2-methanol

To a solution of 1,2,3,4-tetrahydro-7-phenylmethoxy-4-methycyclopent[b]indole-2-carboxylic acid ethyl ester (2.0 g, 0.006 mole) in 50 ml of dry tetrahydrofuran, was added lithium aluminum hydride (1M solution in tetrahydrofuran, 10 ml, 0.01 mole). After stirring at 70° C. for one hour, the mixture was cooled, quenched with 2 ml of saturated ammonium chloride solution, filtered, and the filtrate concentrated to a brown oil, ~2 g. This oil was eluted on a silica gel column with 10% methanol/dichloromethane via HPLC. The desired fractions were combined and concentrated to a tan oil, which solidified on standing to give 1.3 g of the product, m.p. 83°–85° C.

Analysis: Calculated for $C_{20}H_{21}NO_2$: 78.14%C 6.89%H 4.56%N Found: 77.71%C 6.66%H 4.70%N

EXAMPLE 18

1,2,3,4-Tetrahydro-7-methoxy-4-methylcyclopent[b]indole-2-methanamine hydrochloride To a solution of 1,2,3,4-tetrahydro-7-methoxy-4-methylcyclopent[b]indole-2-carboxylic acid amide (2.3 g, 0.009 mole) in 50 ml of dry tetrahydrofuran, was added lithium aluminum hydride (1M solution in tetrahydrofuran, 20 ml, 0.02 mole). After stirring at 70° C. for one hour, the mixture was cooled, quenched with 5 ml of saturated ammonium chloride solution and diluted with 100 ml of ether. The mixture was filtered, and the filtrate concentrated to a yellow oil (~2 g). This oil was dissolved in ether and the pH of the solution adjusted to 1 with ethereal-HCl. The resultant precipitate was collected and dried to give the product as a grey powder, 1.2 g, m.p. 188°–189° C.

Analysis: Calculated for $C_{14}H_{18}N_2O\cdot HCl$: 63.03%C 7.18%H 10.50%N Found: 63.33%C 7.17%H 10.08%N

EXAMPLE 19

1,2,3,4-Tetrahydro-7-phenylmethoxy-4-methylcyclopent[b]indole-2-methanamine hydrochloride To a solution of 1,2,3,4-tetrahydro-7-phenylmethoxy-4-methylcyclopent[b]indole-2-carboxylic acid amide (5.0 g, 0.015 mole) in 100 ml of tetrahydrofuran, was added lithium aluminum hydride (1M solution in tetrahydrofuran, 20 ml, 0.02 mole). After stirring at 70° C. for one hour, the mixture was cooled, quenched with 5 ml of saturated ammonium chloride solution, filtered, and the filtrate concentrated to a brown oil, ~5 g. This oil was eluted on a silica gel column with 10% methanol/dichloromethane via HPLC. The desired fractions were combined and concentrated to a thick yellow oil. 4.1 g. A 0.5 g sample of this oil was dissolved in ether, the pH adjusted to 1 with etheral HCl, and the resultant precipitate collected and dried to give 0.4 g of the product, mp 200° C. (dec.). This material was recrystallized from methanol/ether (1:1) to give the product (0.35 g,), as an off-white solid, mp 232° C. (dec.).

Analysis: Calculated for $C_{20}H_{22}N_2O\cdot HCl$: 70.06%C 6.76%H 8.17%N Found: 69.96%C 6.78%H 8.01%N

EXAMPLE 20

1,2,3,4-Tetrahydro-7-methoxy-N-methylcyclopent[b]indole-2-methanamine maleate

Lithium aluminum hydride solution (27.5 ml, 1.0M in THF, 0.0275 mole) was added dropwise to a solution of 1,2,3,4-tetrahydro-7-methoxy-N-methylcyclopent[b]indol-2-carboxylic acid amide (2.6 g, 0.011 mole) in 80 ml of tetrahydrofuran at ambient temperature. The mixture was heated to 80° C. and stirred for 5 hours. The mixture was quenched with water, and ethyl acetate was added. The mixture was filtered, the filtrate was separated, and the aqueous layer was extracted with ethyl acetate (2×). The combined organic extracts were washed with water and dried (sat. NaCl, anh. MgSO4). After filtering, the solvent was evaporated to yield a light brown solid (2.3 g), which was eluted with 10% methanol in dichloromethane on a silica gel column via flash chromatography. The desired fractions were combined and concentrated to yield a tan solid (1.15 g). The solid was converted to the maleate salt in methanol/ether (1:5) to yield 0.50 g of the product as a white solid, m.p. 142°–143° C.

Analysis: Calculated for $C_{14}H_{18}N_2O\cdot C_4H_4O_4$: 62.42%C 6.40%H 8.09%N Found: 62.46%C 6.36%H 8.30%N

EXAMPLE 21

1,2,3,4-Tetrahydro-7-methoxy-N,4-dimethylcyclopent[b]indole-2-methanamine maleate To a solution of 1,2,3,4-tetrahydro-7-methoxy-N,4-dimethylcyclopent[b]indole-2-carboxylic acid amide (2.0 g, 0,008 mole) in 50 ml of tetrahydrofuran, was added a solution of $LiAlH_4$ (1M in THF, 20 ml, 0.02 mole) in ten minutes. After stirring at 70° C. for two hours, the mixture was cooled, quenched with 5 ml of saturated $NH_4Cl$ solution, and diluted with 100 ml ether. The mixture was filtered, and the filtrate concentrated to a thick yellow oil (1.7 g,). A solution of the oil in ether was adjusted to pH 1 with ethereal maleic acid, and the resultant tan precipitate collected and dried to give 1.3 g of white crystals, mp 125° C. (dec.). Recrystallization from methanol/ether (1:10) gave the product as a white solid (1.2 g), mp 129° C. (dec.).

Analysis: Calculated for $C_{15}H_{20}N_2O\cdot C_4H_4O_4$: 63.32%C 6.71%H 7.77%N Found: 63.18%C 6.67%H 7.95%N

EXAMPLE 22

1,2,3,4-Tetrahydro-7-phenylmethoxy-N,4-dimethylcyclopent[b]indole-2-methanamine hydrochloride To a solution of 1,2,3,4-tetrahydro-7-phenylmethoxy-N,4-dimethylcyclopent[b]indole-2-carboxylic acid amide (2.6 g, 0.008 mole) in 50 ml of tetrahydrofuran, was added a solution of lithium aluminum hydride (1M in tetrahydrofuran, 16 ml, 0.016 mole). After stirring at 70° C. for one hour, the mixture was cooled, quenched with 5 ml of saturated ammonium chloride solution, and diluted with 100 ml of ether. After filtering, the filtrate was concentrated to a yellow oil, which was dissolved in ether and the solution acidified to pH 1 with ethereal HCl. The resultant precipitate was collected and dried to give 1.9 g of a solid, m.p. 222° C. (dec.). This material was recrystallized from methanol/ether (1:1) to give the product as a pale yellow solid, 1.7 g, m.p. 250° C. (dec.).

Analysis: Calculated for $C_{21}H_{24}N_2O\cdot HCl$: 70.67%C 7.06%H 7.85%N Found: 70.39%C 7.19%H 7.48%N

EXAMPLE 23

1,2,3,4-Tetrahydro-4-methyl-2-[methylamino)methyl]-cyclopent[b]indol-7-ol hydrochloride In a Parr hydrogenation bottle was suspended 0.5 g of 10% palladium on carbon in 50 ml of ethanol, and to this suspension was added a suspension of 1,2,3,4-tetrahydro-7-phenylmethoxy-N,4-dimethylcyclopent[b]indole-2-methanamine hydrochloride (1.1 g, 0.008 mole) in 200 ml of ethanol. After shaking at 50° C. under 50 psi of hydrogen for one hour, the solution was cooled and filtered, and the filtrate concentrated to a gray solid, 0.8 g, m.p. 229° C. (dec.). This material was recrystallized from methanol to give the product as an off-white solid, 0.6 g, m.p. 230° C. (dec.).

Analysis: Calculated for $C_{14}H_{18}N_2O \cdot HCl$: 63.03%C 7.18%H 10.50%N Found: 63.07%C 7.03%H 10.25%N

EXAMPLE 24

1,2,3,4-Tetrahydro-4-methyl-2-[(methylamino)methyl]-cyclopent[b]indol-7-yl methylcarbamate To a solution of 1,2,3,4-tetrahydro-4-methyl-2-[(methylamino)methyl]cyclopent[b]indol-7-ol (1.7 g, 0.007 mole) in 30 ml of tetrahydrofuran, was added milled $K_2CO_3$ (1.2 g, 0.01 mole), followed by methyl isocyanate (0.4 ml, 0.07 mole). After stirring at ambient temperature for two hours, the mixture was filtered, and the filtrate concentrated to a yellow oil (~2 g), which was dissolved in ethyl acetate then washed with water and then dried over anhydrous $MgSO_4$. After filtering, the solvent was evaporated to afford a tan solid, ~1.0 g, which was eluted on a silica gel column with 5% methanol/dichloromethane via HPLC. The desired fraction was concentrated to a tan foam (0.8 g, m.p. ~50° C.), which was recrystallized from ethyl ether to give the product as a tan solid, 0.6 g, m.p. 216° C. (dec).

Analysis: Calculated for $C_{16}H_{21}N_3O_2$: 66.87%C 7.37%H 14.62%N Found: 66.84%C 7.39%H 14.21%N

EXAMPLE 25

1,2,3,4-Tetrahydro-7-methoxy-N,N4-trimethycyclopent[b]-2-methanamine hydrochloride To a solution of 1,2,3,4-tetrahydro-7-methoxy-N,N,4-trimethylcyclopent[b]indole2-carboxylic acid amide (0.8 g, 0.003 mole) in 25 ml of tetrahydrofuran, was added a solution of lithium aluminum hydride (1M solution in THF, 6 ml, 0.006 mole). After stirring at 70° C. for one hour, the mixture was cooled, diluted with ether, and quenched with 2 ml of saturated $NH_4Cl$ solution. The mixture was filtered, and the filtrate acidified to pH 1 with ethereal HCl. The resultant tan precipitate was collected and dried to give 0.8 g, of a solid, m.p. 215° C. (dec.). This material was recrystallized from methanol/ether (1:1) to give the product as white crystals, 0.6 g, m.p. 215° C. (dec.).

Analysis: Calculated for
$C_{16}H_{22}N_2O \cdot HCl$: 65.18%C 7.86%H 9.50%N Found: 64.92%C 7.85%H 9.38%N

EXAMPLE 26

1,2,3,4-Tetrahydro-7-phenylmethoxy-N,N,4-trimethyl-cyclopent[b]indole-2-methanamine hydrochloride To a solution of 1,2,3,4-tetrahydro-7-phenylmethoxy-N,4-dimethylcyclopent[b]indole-2-methanamine (6.4 g, 0.02 mole) in 70 ml of dimethylformamide, was added sodium hydride (60% in oil, 0.8 g, 0.02 mole). After stirring at ambient temperature for 1 hour, a solution of methyl iodide (1.2 ml, 0.02 mole) in 5 ml of dimethylformamide was added, and the mixture stirred at 70° C. for 3 hours. After cooling, the mixture was poured into 300 ml of water, stirred for 5 minutes, and then extracted with ethyl acetate (3×). The organic layer was washed successively with water and a saturated sodium chloride solution, and thereafter dried over anhydrous $MgSO_4$. After filtering, the solvent was removed by evaporation to afford an oil, 6.4 g, which was eluted on a silica gel column with 5% methanol/dichloromethane via HPLC. The desired fractions were combined and concentrated to a thick oil, 3.1 g. A 1.0 g portion of this oil was dissolved in ether, and the pH was adjusted to 1 with ethereal HCl. The resultant white precipitate was collected and dried to give 1.0 g of solid, m.p. 155°–165° C. This material was recrystallized from methanol/ether (1:3) to give the product as white crystals, 0.8 g, m.p. 185° C. (dec.)

Analysis: Calculated for $C_{22}H_{26}N_2O \cdot HCl$: 71.23%C 7.34%H 7.55%N Found: 71.10%C 7.49%H 7.42%N

EXAMPLE 27

1,2,3,4-Tetrahydro-4-methyl-2-[(dimethylamino)methyl]cyclopent [b]indole-7-ol

In a 500 ml Parr hydrogenation bottle was suspended 0.5 g of 10% Pd/C in 50 ml of ethyl alcohol. To this was added a solution of 1,2,3,4-tetrahydro-7-phenylmethoxy-N,N,4-trimethylcyclopent[b]indole-2-methanamine (2.3 g, 0.007 mole) in 200 ml of ethyl alcohol. After shaking at 50° C. under 50 psi hydrogen for two hours, the mixture was cooled and filtered, and the filtrate concentrated to a tan solid, 1.5 g, m.p. 110° C.

EXAMPLE 28

1,2,3,4-Tetrahydro-2-[(dimethylamino)methyl]-4-methylcyclopent[b]indol-7-yl-methylcarbamate hydrochloride To a solution of 1,2,3,4-tetrahydro-2-[(dimethylamino)methyl]-4methylcyclopent[b]indol-7-ol (1.5 g, 0,006 mole) in 50 ml of tetrahydrofuran, was added milled $K_2CO_3$ (1.7 g, 0.012 mole), followed by methyl isocyanate (0.34 ml, 0.006 mole). After stirring at ambient temperature for 20 hours, the mixture was filtered, and the filtrate concentrated to an oil, 1.7 g. This oil was eluted on a silica gel column with 25% methanol/dichloromethane via HPLC. The desired fractions were combined and concentrated to a thick oil, 1.3 g, which was dissolved in ether. The pH was adjusted to 1 with ethereal HCl, and the resultant white precipitate was collected and dried to give a solid, 1.2 g, m.p. 210° C. (dec.) This material was recrystallized from methanol/ether (1:3) to give the product as white crystals, 1.1 g, m.p. 210° C. (dec.)

Analysis: Calculated for $C_{17}H_{23}N_3O_2 \cdot HCl$: 60.43%C 7.16%H 12.44%N Found: 60.19%C 7.18%H 12.39%N

EXAMPLE 29

1,2,3,4-Tetrahydro-4-methyl-7-methoxy-N-ethylcyclopent[b]indole-2-methanamine maleate To a solution of 1,2,3,4-tetrahydro-4-methyl-7-methoxy-N-ethylcyclopent[b]indole-2-carboxylic acid amide (0.8 g, 0.003 mole) in 50 ml of dry tetrahydrofuran was added a solution of lithium aluminum hydride (1M solution in THF, 5 ml, 0.005 mole). After stirring at 70° C. for two hours, the mixture was cooled, quenched with 3 ml of saturated ammonium chloride solution, diluted with 100 ml of ether, and then filtered. The filtrate was concentrated to a yellow oil (~0.6 g) which was dissolved in ether. The pH was adjusted to 1 with ethereal maleic acid, and the resultant tan precipitate was collected and dried to give 0.6 g of a solid, m.p. 135°–136° C. Recrystallization from methanol/ether (1:20) gave the product as an off-white solid, 0.5 g, m.p. 141°–142° C.

Analysis: Calculated for $C_{16}H_{22}N_2O \cdot C_4H_4O_4$: 64.15%C 7.00%H 7.48%N Found: 64.06%C 6.92%H 7.44%N

EXAMPLE 30

1,2,3,4-Tetrahydro-7-methoxy-N-propylcyclopent[b]indole-2-methanamine maleate

Lithium aluminum hydride solution (48 ml, 1M solution in THF, 0.048 mole) was added dropwise, to a solution of 1,2,3,4-tetrahydro-7-methoxy-N-propylcyclopent[b]indol-2-carboxylic acid amide (5.25 g, 0,019 mole) in 100 ml of tetrahydrofuran at ambient temperature. The mixture was heated to 70° C. and stirred for 12 hours. The reaction mixture was quenched with water and ethyl acetate was added. After stirring for 10 minutes, the mixture was filtered, the filtrate separated, and the aqueous layer was extracted with ethyl acetate (2×). The combined organic phase was washed with water and dried (anh. MgSO$_4$). After filtering, the solvent was evaporated to yield a yellow solid (4.4 g), which was eluted with 10% methanol in CH$_2$Cl$_2$ on a silica gel column via HPLC. The desired fractions were concentrated to yield a tan solid (2.91 g). A 1.0 g portion was converted to the maleate salt in methanol/ether (1:5) to yield 0.87 g of the product as a white solid, m.p. 160°–162° C.

Analysis: Calculated for $C_{16}H_{22}N_2O \cdot C_4H_4O_4$: 64.15%C 7.00%H 7.48%N Found: 64.32%C 7.24%H 7.50%N

EXAMPLE 31

1,2,3,4-Tetrahydro-N,4-dimethyl-N-propyl-7-methoxycyclopent[b]indole-2-methanamine To a solution of 1,2,3,4-tetrahydro-N-propyl-7-methoxycyclopent[b]indole-2-methanamine (1.5 g, 0,006 mole) in 20 ml of dimethylformamide was added sodium hydride (60% in oil, 0.5 g, 0,012 mole). After stirring at ambient temperature for two hours, a solution of methyl iodide (0.7 ml, 0.012 mole) in 5 ml of dimethylformamide was added, and the mixture was stirred at 70° C. for five hours. After cooling, the mixture was poured into 100 ml of water, stirred for five minutes, and then extracted with ethyl acetate (2×). The organic layer was washed successively with water and saturated NaCl solution, and then dried over anhydrous MgSO$_4$. After filtering, the solution was concentrated to a brown oil (~2 g), which was eluted on a silica gel column with 5% methanol/dichloromethane via HPLC, to afford the product as a thick yellow oil (1.1 g).

Analysis: Calculated for $C_{18}H_{26}N_2O$: 75.48%C 9.15%H 9.78%N Found: 74.99%C 9.29%H 9.46%N

EXAMPLE 32

1,2,3,4-Tetrahydro-2-hydroxymethyl-4-methylcyclopent[b]indole-7-ol

To a suspension of 10% Pd/C (1.2 g) in 50 ml of ethanol was added a solution of 1,2,3,4-tetrahydro-7-phenylmethoxy-4-methylcyclopent[b]indole-2-methanol (8.4 g, 0.027 mole) in 200 ml of ethanol in a Parr hydrogenation bottle. After shaking at 50° C., under 50 psi hydrogen for two hours, the mixture was cooled, filtered, and then concentrated to a dark oil. The oil was eluted on a silica gel column with ethyl acetate/dichloromethane (1:2) via HPLC. The desired fractions were combined and then concentrated to a light yellow solid. The material was triturated with ether and dried to give 4.0 g (66%) of the product as an off-white solid, m.p. 153°–4° C.

Analysis: Calculated for $C_{13}H_{15}NO_2$: 71.86%C 6.96%H 6.45%N Found: 71.42%C 6.96%H 6.13%N

EXAMPLE 33

1,2,3,4-Tetrahydro-2-hydroxymethyl-4-methylcyclopent[b]indol-7-yl methylcarbamate To a solution of 1,2,3,4-tetrahydro-2-hydroxymethyl-4-methylcyclopent[b]indol-7-ol (1.7 g, 0.008 mole) in 50 ml of tetrahydrofuran was added milled K$_2$CO$_3$ (2.0 g, 0.015 mole), followed by a solution of methylisocyanate (0.5 ml, 0.008 mole) in 5 ml of tetrahydrofuran. After stirring at ambient temperature for two hours, the mixture was filtered and the filtrate concentrated to a yellow solid. This material was eluted on a silica gel column with ethyl acetate/dichloromethane (1:2) via HPLC. The desired fractions were combined and concentrated to a white solid, 2.1 g, m.p. 134°–8° C. This material was recrystallized from methanol/ether (1:10) to give the product as a white solid, 1.5 g, m.p. 137°–8° C.

Analysis Calculated for $C_{15}H_{18}N_2O_3$: 65.67%C 6.61%H 10.21%N Found: 65.60%C 6.60%H 10.14%N

EXAMPLE 34

4-Methyl-7-phenoxymethyl-1,2,3,4-tetrahydrocyclopent[b]indole-2-methanol methanesulfonate To a solution of 1,2,3,4-tetrahydro-7-phenylmethoxy-4-methylcyclopent[b]indole-2-methanol (11.2 g, 0.036 mole) and triethylamine (3.39 g, 0.047 mole) and 220 ml of dichloromethane (anhydrous) was added a solution of methanesulfonyl chloride (5.38 g, 0.047 mole) in 27 ml of dichloromethane. After stirring at ambient temperature for 2 hours, additional triethylamine (3.39 g, 0,047 mole) was added, followed by a solution of methanesulfonyl chloride (5.38 g, 3.6 ml, 0,047 mole) in 30 ml of dichloromethane. After stirring for one hour, the mixture was poured into 500 ml of water. The phases were separated and the dichloromethane portion was washed successively with water and saturated sodium chloride solution. The organic phase was dried (anh. MgSO$_4$) and filtered, and the filtrate was concentrated to a dark green oil (15 g). This oil was eluted on silica gel with ethyl acetate/dichloromethane (1:19) via HPLC. The desired fractions were combined and concentrated to give the product as a white solid, 6.27 g, mp. 94°–96° C.

Analysis: Calculated for $C_{21}H_{23}NO_4S$: 65.43%C 6.01%H 3.63%N Found: 65.22%C 5.98%H 3.45%N

EXAMPLE 35

4-Methyl-7-phenylmethoxy-1,2,3,4tetrahydrocyclopent[b]indole-2-acetonitrile

To a solution of 4-methyl-7-phenoxymethyl-1,2,3,4-tetrahydrocyclopent[b]indole-2-methanol methanesulfonate (8.7 g, 0.023 mole) in 150 ml of dimethylsulfoxide was added a solution of sodium cyanide (1.3 g, 0.0265 mole) in 110 ml of dimethylsulfoxide. The solution was stirred at 100° C. for five hours, cooled and stirred with ice water (500 ml). The aqueous solution was extracted with dichloromethane (2×500 ml) and the combined dichloromethane phase was washed successively with water and saturated sodium chloride solution. The dried (anh. MgSO₄) organic phase was filtered and the filtrate concentrated to a red oil (10 g), which was eluted on silica gel with dichloromethane via HPLC. The desired fractions were combined and concentrated to give the product as a white solid (6.27g), mp 104°–105° C.

Analysis: Calculated for C₂₁H₂₀N₂O: 79.71%C 6.37%H 8.86%N Found: 79.39%C 6.45%H 8.71%N

EXAMPLE 36

1,2,3,4-Tetrahydro-7-phenylmethoxy-4-methylcyclopent[b]indole-2-ethaneamine

A solution of 4-methyl-7-phenylmethoxy-1,2,3,4-tetrahydrocyclopent[b]indole-2-acetonitrile (3.7 g, .0117 mole) in 250 ml of tetrahydrofuran was cooled to −9° C. with an ice/salt bath and 1 molar solution of lithium aluminum hydride in tetrahydrofuran (14 ml, 0.014 mol) was added. The temperature was allowed to rise slowly while stirring for 1 hour. Excess lithium aluminum hydride was neutralized with a saturated ammonium chloride solution. The tetrahydrofuran solution was filtered and the filtrate was concentrated to a yellow solid (4 g). This material was eluted on silica gel with methanol/dichloromethane (1:6) via HPLC. The appropriate fractions were combined and concentrated to give the product as a pale yellow solid, 2.5 g, mp 72°–75° C.

Analysis: Calculated for C₂₁H₂₄N₂O: 78.71%C 7.55%H 8.74%N Found: 78.51%C 7.47%H 8.54%N

We claim:

1. A compound of the formula

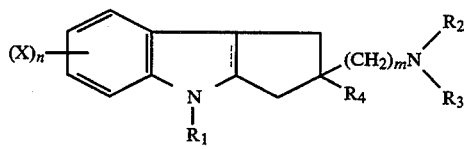

where,

R₁ is H, loweralkyl, arylloweralkyl or loweralkylcarbonyl;

R₂ is H, loweralkyl, aryl, arylloweralkyl or loweralkylcarbonyl;

R₃ is H or loweralkyl;

R₄ is H;

m is an integer of 1 or 2;

n is an integer of 1 or 2; and

X is loweralkoxy, arylloweralkoxy, hydroxy,

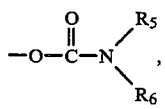

amino loweralkyamine, diloweralkylamino, loweralkylcarbonylamino or loweralkoxycarbonylamino, wherein R₅ is H or loweralkyl; and R₆ is H loweralkyl, arylloweralkyl or aryl; or alternatively the group —NR₅R₆ as a whole is

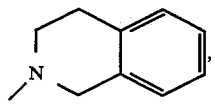

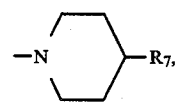

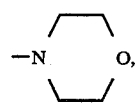

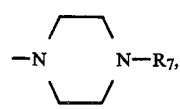

R₇ being hydrogen or loweralkyl; or a pharmaceutically acceptable acid addition salt thereof.

2. The compound as defined in claim 1, where R₄ is hydrogen.

3. The compound as defined in claim 1, where n is 1.

4. The compound as defined in claim 1, where R₁ is hydrogen or methyl.

5. The compound as defined in claim 1, where R₄ is hydrogen and n is 1.

6. The compound as defined in claim 1, which is 1,2,3,4-tetrahydro-7-methoxy- 4-methylcyclopent[b]indole-2-methanamine.

7. The compound as defined in claim 1, which is 1,2,3,4-tetrahydro-7-phenylmethoxy-4-methylcyclopent[b]indole-2-methanamine.

8. The compound as defined in claim 1, which is 1,2,3,4-tetrahydro-7-methoxy-N-methylcyclopent[b]indole-2-methanamine.

9. The compound as defined in claim 1, which is 1,2,3,4-tetrahydro-7-methoxy-N, 4-dimethylcyclopent[b]indole- 2-methanamine.

10. The compound as defined in claim 1, which is 1,2,3,4-tetrahydro-7-phenylmethoxy-N,4-dimethylcyclopent[b]indole -2-methanamine.

11. The compound as defined in claim 1, which is 1,2,3,4-tetrahydro-4-methyl-2-[(methylamino)methyl]-cyclopent[b]indol- 7-ol.

12. The compound as defined in claim 1, which is 1,2,3,4-tetrahydro-4-methyl-2-[(methylamino)methyl]-cyclopent[b]indol-7-yl methylcarbamate.

13. The compound as defined in claim 1, which is 1,2,3,4-tetrahydro-7-methoxy- N,N ,4-trimethylcyclopent[b]indole-2-methanamine.

14. The compound as defined in claim 1, which is 1,2,3,4-tetrahydro -7-phenylmethoxy- N,N,4-trimethylcyclopent[b]indole- 2-methanamine.

15. The compound as defined in claim 1, which is 1,2,3,4-tetrahydro-4-methyl-2-[(dimethylamino)methyl]cyclopent[b]indole-7-ol.

16. The compound as defined in claim 1, which is 1,2,3,4-tetrahydro-2-[(dimethylamino)methyl]-4-methylcyclopent[b]indol-7-yl methylcarbamate.

17. The compound as defined in claim 1, which is 1,2,3,4-tetrahydro-4-methyl -7-methoxy-N-ethylcyclopent[b]indole-2-methanamine.

18. The compound as defined in claim 1, which is 1,2,3,4-tetrahydro-7-methoxy-N -propylcyclopent[b]indole-2-methanamine.

19. The compound as defined in claim 1, which is 1,2,3,4,-tetrahydro-N,4-dimethyl- N-propyl-7-methoxycyclopent[b]indole-2-methanamine.

20. The compound as defined in claim 1, which is 1,2,3,4-tetrahydro-7-phenylmethoxy-4-methylcyclopent[b]indole-2-ethaneamine.

21. A pharmaceutical composition comprising a compound as defined in claim 1 in an amount effective for alleviating depression and a suitable carrier therefor.

22. A pharmaceutical composition comprising a compound as defined in claim 1 in an amount effective for alleviating a memory dysfunction characterized by a cholinergic deficit and a suitable carrier therefor.

23. A method of treating a patient in need of relief from depression which comprises administering the patient an effective amount of a compound as defined in claim 1.

24. A method of treating a patient in need of relief from a memory dysfunction characterized by a cholinergic deficit which comprises administering the patient an effective amount of a compound as defined in claim 1.

* * * * *